United States Patent [19]

Uchiyama et al.

[11] Patent Number: 5,463,123
[45] Date of Patent: Oct. 31, 1995

[54] PROCESS FOR PRODUCING α-HYDROXYISOBUTYRAMIDE

[75] Inventors: Takako Uchiyama; Hirofumi Higuchi, both of Niigata, Japan

[73] Assignee: Mitsubishi Gas Chemical Company, Inc., Tokyo, Japan

[21] Appl. No.: 135,062

[22] Filed: Oct. 12, 1993

[30] Foreign Application Priority Data

Nov. 9, 1992 [JP] Japan .................................. 4-298781

[51] Int. Cl.$^6$ .................................................. C07C 231/06
[52] U.S. Cl. .......................... 564/126; 564/124; 564/127; 564/128; 502/324
[58] Field of Search ............................ 564/126, 128, 564/125, 124, 127; 502/324

[56] References Cited

U.S. PATENT DOCUMENTS

| | | | |
|---|---|---|---|
| 4,018,829 | 4/1977 | Gruber et al. | 564/126 |
| 4,329,500 | 5/1982 | Habermann | 564/126 |
| 4,820,872 | 4/1989 | Farrar et al. | 564/126 |
| 4,950,801 | 8/1990 | Ebata et al. | 564/126 |
| 4,987,256 | 1/1991 | Ebata et al. | 564/126 |

FOREIGN PATENT DOCUMENTS

| | | |
|---|---|---|
| 0418512A1 | 3/1991 | European Pat. Off. . |
| 0433611 | 6/1991 | European Pat. Off. ............... 564/126 |
| 2527120 | 12/1976 | Germany . |

OTHER PUBLICATIONS

Chemical Abstracts, vol. 117, No. 1, 1992, Columbus, Ohio, US; Abstract No. 7527v. Preparation of Alpha-Hydroxysobutyramide, p. 763, of JP-A-4 046 145.
Chemical Abstracts, vol. 118, No. 11, 1993, Columbus, Ohio, US; Abstract No. 101522g, Preparation of Alpha-Hydroxyisobutyramide p. 804, of JP-A-4-282 352.

Primary Examiner—Shailendra Kumar
Attorney, Agent, or Firm—Frishauf, Holtz Goodman, Langer & Chick

[57] ABSTRACT

There is disclosed a process for producing α-hydroxyisobutyramide by hydration reaction of acetone cyanohydrin in the presence of a catalyst consisting essentially of manganese dioxide which process comprises pretreating the catalyst with a reducing agent. The above process is capable of eliminating the catalyst clogging trouble due to the deposition of the by-produced oxamide and thus proceeding with long-term reaction with the stabilized catalyst performance.

22 Claims, No Drawings

PROCESS FOR PRODUCING α-HYDROXYISOBUTYRAMIDE

BACKGROUND OF THE INVENTION

1. Field of the Invention

The present invention relates to a process for industrially producing α-hydroxyisobutyramide by the hydration reaction of acetone cyanohydrin. α-Hydroxyisobutyramide is an industrially useful substance which serves as an intermediate starting material for methacrylamide and methyl methacrylate.

2. Description of the Related Arts

It is publicly known that manganese dioxide is used as a solid catalyst in the hydration reaction of acetone cyanohydrin. According to any of the conventional processes, α-hydroxyisobutyramide is obtained by the reaction of acetone cyanohydrin with water as shown by the following reaction equation at a temperature of 40° to 100° C. in the presence of manganese-based catalyst and preferably an acetone-based solvent in a yield of 60 to 95%.

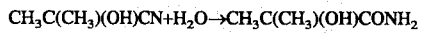

However, the actual result of the hydration reaction thereof by the use of the publicly known manganese-based catalyst involves serious problems from the viewpoint of stable operation in an industrial scale due to the disadvantages that the product α-hydroxyisobutyramide is obtained in low yield with unsatisfactory reaction achievement and catalyst activity deteriorates with the elapse of time even in the case of high performance in the initial stage of the reaction, thereby lowering the yield of the product. The present inventors have already found that the catalyst comprising, as the essential component, manganese dioxide prepared under specific conditions (hereinafter referred to as "modified manganese catalyst") is effective and such catalyst has been disclosed in Japanese Patent Application Laid-Open No.93761/1991. Although the modified manganese catalyst prepared under the specific conditions has an extremely high activity and a long service life, it has been proved that the use thereof as a fixed-bed catalyst in a solid-liquid contact reaction process causes a white crystal to deposit at the inlet and on the downstream side of the catalyst packing section from the start of the reaction to the relatively initial stage thereof depending upon the reaction condition, thus raising the trouble of clogging the catalyst bed.

SUMMARY OF THE INVENTION

It is an object of the present invention to provide a method of solving such trouble of clogging in the catalyst bed when the modified manganese catalyst is used in the bed.

Under such circumstances, intensive research and investigation were made by the present inventors in order to solve the clogging trouble in the aforesaid catalyst bed. As a result, it has been found by the present inventors that the white crystal which was deposited in the beginning of the synthetic reaction of acetone cyanohydrin with water into α-hydroxyisobutyramide in the presence of the modified manganese catalyst was sparingly soluble in water and organic solvents and that it was an oxamide. It was thought that the oxamide was formed through the steps wherein acetone cyanohydrin is decomposed to form hydrogen cyanide, which is oxidized into dicyanides, followed by further hydration.

As a result of further investigation continued by the present inventors on the basis of the above-mentioned finding and information, it has been discovered that the by-production of the white crystal can be suppressed and thus the clogging trouble can be eliminated by adopting a method which comprises pretreating the modified manganese catalyst with a reducing liquid prior to the start of the reaction, thereby weakening only the oxidation capability of the catalyst, while preserving the hydration capacity thereof as it is. The above-mentioned discovery led to success in accomplishing the present invention.

Specifically the present invention relates to a process for producing α-hydroxyisobutyramide by hydration reaction of acetone cyanohydrin in the presence of a catalyst consisting essentially of manganese dioxide which process comprises treating said catalyst in advance with a reducing liquid.

DESCRIPTION OF PREFERRED EMBODIMENT

In the following, the specific embodiment to carry out the present invention will be described.

As the reaction method in the present invention, there is applied a continuous flow reaction method using a fixed-bed catalyst which is well suited to industrial mass production. The modified manganese catalyst to be used as the fixed-bed catalyst is applied in lump a or in the form of molding by tabletting or extrusion.

The pretreatment of the modified manganese catalyst by means of a reducing liquid according to the present invention can be put into practice separately prior to its packing in a reactor, but is preferably carried out after its packing in the reactor and prior to feeding a starting raw liquid from the industrial standpoint.

As the reducing liquid, that is, the pretreating agent in the present invention, there is effectively usable a reductive substance exemplified by an alcohol such as methanol, ethanol and propanol; an aldehyde such as formaldehyde, acetaldehyde and propionaldehyde; a ketone such as acetone and methyl ethyl ketone; formic acid; and hydrogen peroxide. The above-exemplified reducing liquid can be employed alone or in combination with at least one other reducing liquid. The reducing liquid can be employed in the form of an aqueous solution, if necessary.

The pretreating temperature with the reducing liquid according to the present invention is usually in the range of room temperature to 80° C. but should be determined in accordance with the kind and concentration of the reducing liquid to be employed. The pretreating time with the reducing liquid is not specifically limited but is preferably in the range of 0.1 to 48 hours from the viewpoint of industrial practice.

The hydration reaction temperature of acetone cyanohydrin according to the present invention is in the range of 30° to 100° C., preferably 40° to 80° C. A reaction temperature lower than 30° C. undesirably lowers the rate of the reaction, whereas that higher than 100° C. unfavorably increases the byproduct due to the decomposition of the acetone cyanohydrin. The reaction pressure is preferably selected so as to maintain the reaction system in liquid phase usually in the range of atmospheric pressure to not higher than 2 kg/cm²G, taking into consideration the hydration reaction being liquid-phase reaction.

The hydration reaction according to the present invention is put into practice in the reaction system containing usually an excess of water. The content of acetone cyanohydrin in the starting raw liquid is 10 to 60%, preferably 20 to 50% by weight. The presence of acetone in the starting raw liquid in an amount of 5 to 30% by weight is effective in that the decomposition of the acetone cyanohydrin as the side reaction is suppressed thereby, resulting in an increase in the yield of the α-hydroxyisobutyramide as the objective product.

The process according to the present invention can supress the byproduction of oxamide and thereby eliminate the clogging in the catalyst bed by pretreating the catalyst consisting essentially of manganese dioxide in advance with the reducing agent in the synthetic reaction of acetone cyanohydrin with water into the objective α-hydroxyisobutyramide in the presence of the catalyst, thus rendering itself extremely significant from the industrial standpoint.

In the following, the present invention will be described in more detail with reference to examples and comparative examples, which however, are not to be construed to limit the invention thereto.

EXAMPLE 1

1) Preparation of catalyst:

To a solution of 66.4 g of potassium permanganate in 580 g of water was promptly added at 70° C., a mixture of 138.7 g of an aqueous solution of manganese sulfate containing 14% by weight of Mn, 2.91 g of stannous sulfate, 23.9 g of conc. sulfuric acid and 20 g of water. The resultant precipitate was aged at 90° C. for 3 hours and then filtered. The resultant cake was washed with one (1) liter of water four times and was dried overnight at 110° C. to provide 68.2 g of modified manganese dioxide.

2) Pretreatment:

A jacketed pyrex-made tubular reactor having 10 mm inside diameter and 20 cm length was packed with 4 g of the catalyst consisting of the modified manganese dioxide which had been obtained in the preceding item 1) and arranged to 30 to 60 mesh by crushing, and warm water at 50° C. was allowed to pass through the jacket. Subsequently 20% by weight of aqueous solution of acetone was fed to the catalyst thus packed at a rate of 4 g/hour for 12 hours.

3) Reaction:

A mixed starting raw solution containing 40 g of acetone cyanohydrin, 50 g of water and 10 g of acetone was fed to the reactor at the upper part thereof at a feed rate of 5 g/hour. A measurement was made of the concentration of oxamide in the reaction liquid every 0.5 hour. As the result, the concentration reached the maximum value of 500 ppm after two hours from the start of the reaction and thereafter gradually decreased as low as 30 ppm after 5 hours. Deposit of white crystal was not observed in the catalyst-packed bed throughout the reaction.

In addition, the reaction solution was collected and analyzed after 5 hours from the start of the reation. As the result, the objective α-hydroxyisobutyramide was obtained in 95% yield. Thereafter, long-term stable reaction was possible to continue with stabilized catalyst performance.

COMPARATIVE EXAMPLE 1

The procedure in Example 1 was repeated except that the pretreatment by the use of 20% by weight of the aqueous solution of acetone was omitted. As a result, white crystal began to deposit in the catalyst-packed part after about one (1) hour from the start of the reaction, the reaction solution was made non-smooth to pass through the reactor after 3 hours and finally the reaction was made impossible to continue after 5 hours.

In addition, measurements were made of the solubilities of oxamide in water and the reaction solution, respectively at 50° C. As the result, it was proved that oxamide in a concentration of 1,000 ppm or higher caused its crystal to deposit, thus failing to dissolve completely. Accordingly, it was presumed that oxamide in a concentration of 1,000 ppm or higher had been produced in the procedure of Comparative Example 1.

EXAMPLES 2 TO 5

The procedure of Example 1 was repeated except that the pretreatment was carried out by the use of a reducing liquid other than aqueous solution of acetone. Table 1 gives oxamide concentration in the reaction solution after 2 hours from the start of the reaction as well as the yield of the objective α-hydroxyisobutyramide after 5 hours therefrom.

It was possible in any of the Examples 2 to 5 to continue long-term stable reaction after 5 hours and thereafter with stabilized catalyst performance.

TABLE 1

| Example No. | Reducing liquid | Aqueous solution concentration, % by weight | Pretreatment temperature, °C. | Pretreatment time, hour | HIBA yield after 5 hours, % | Oxamide concentration after 2 hours, ppm |
| --- | --- | --- | --- | --- | --- | --- |
| 2 | aqueous solution of methanol | 20 | 50 | 4 | 93 | 30 |
| 3 | aqueous solution of formaldehyde | 5 | 30 | 10 | 89 | 50 |
| 4 | aqueous solution of formic acid | 5 | 25 | 5 | 91 | 380 |
| 5 | aqueous solution of hydrogen peroxide | 5 | 25 | 5 | 95 | 500 |

Remark: HIBA in the table designates α-hydroxyisobutyramide.

What is claimed is:

1. A process for producing α-hydroxyisobutyramide comprising:
   (a) treating a manganese dioxide-containing catalyst with a reducing liquid to weaken the oxidation capability of said catalyst, while preserving the hydration capacity of said catalyst; and then
   (b) carrying out a hydration reaction with a reaction mixture of acetone cyanohydrin in the presence of said catalyst from step (a) in a continuous flow reaction method with a fixed bed of said catalyst.

2. The process according to claim 1 wherein the reducing liquid is at least one member selected from the group consisting of an alcohol, an aldehyde and a ketone.

3. The process according to claim 1 wherein the reducing liquid is an aqueous solution of at least one member selected from the group consisting of an alcohol, an aldehyde and a ketone.

4. The process according to claim 1 wherein the reducing liquid is at least one member selected from the group consisting of methanol, formaldehyde, acetaldehyde and acetone.

5. The process according to claim 1 wherein the reducing liquid is formic acid or an aqueous solution of formic acid.

6. The process according to claim 1 wherein the reducing liquid is an aqueous solution of hydrogen peroxide.

7. The process according to claim 1 wherein said acetone cyanohydrin is contained in an amount of 10 to 60% by weight and said acetone is contained in an amount of 5 to 30% by weight.

8. The process according to claim 1 wherein said catalyst is packed in a reactor for the hydration reaction of acetone cyanohydrin and thereafter said catalyst is pretreated with a reducing liquid.

9. The process according to claim 1 wherein said catalyst is treated with said reducing liquid at a treatment temperature of room temperature to 80° C.

10. The process according to claim 1 wherein said catalyst is treated with said reducing liquid for a pretreatment time of 0.1 to 48 hours.

11. The process according to claim 1 wherein said catalyst is treated with said reducing liquid under a pressure which maintains the reaction mixture in a substantial liquid-phase.

12. The process according to claim 2 wherein the reducing liquid is at least one member selected from the group consisting of methanol, formaldehyde, acetaldehyde and acetone.

13. The process according to claim 1 wherein said reducing liquid is selected from the group consisting of methanol, ethanol, propanol, formaldehyde, acetaldehyde, propionaldehyde, acetone, methylethyl ketone, formic acid and hydrogen peroxide.

14. The process according to claim 13 wherein said acetone cyanohydrin is contained in an amount of 10 to 60% by weight and said acetone is contained in an amount of 5 to 30% by weight.

15. The process according to claim 14 wherein said catalyst is treated with the reducing liquid at a treatment temperature of 40° to 80° C.

16. The process according to claim 14 wherein said catalyst is treated with said reducing liquid for a treatment time of 0.1 to 48 hours.

17. The process according to claim 15 wherein said catalyst is treated with said reducing liquid for a treatment time of 0.1 to 48 hours.

18. The process according to claim 17 wherein said catalyst is treated with said reducing liquid under a pressure which maintains the reaction mixture in a substantial liquid phase.

19. The process according to claim 18 wherein the pressure is not higher than 2 kg/cm$^2$G.

20. The process according to claim 19 wherein said acetone cyanohydrin is contained in an amount of 20 to 50% by weight.

21. The process according to claim 1, wherein acetone is present in step (b).

22. The process according to claim 1, wherein the catalyst contains tin.

* * * * *